United States Patent [19]

Brunner et al.

[11] Patent Number: 4,508,560
[45] Date of Patent: Apr. 2, 1985

[54] CERTAIN PYRIDYLACETYLENE COMPOUNDS, COMPOSITIONS CONTAINING SAME AND HERBICIDAL METHODS OF USE

[75] Inventors: Hans-Georg Brunner, Lausen; Rolf Schurter, Binningen; Henry Szczepanski, Wallbach, all of Switzerland

[73] Assignee: Ciba Geigy Corporation, Ardsley, N.Y.

[21] Appl. No.: 439,456

[22] Filed: Nov. 5, 1982

[30] Foreign Application Priority Data

Nov. 11, 1981 [CH] Switzerland .................. 7257/81

[51] Int. Cl.³ .................... C07D 409/06; A01N 43/40
[52] U.S. Cl. ............................. 71/94; 71/92; 546/284; 546/300; 546/304; 544/238; 544/331; 544/336
[58] Field of Search ................ 546/284; 71/94

[56] References Cited

PUBLICATIONS

Brunner et al., Chemical Abstracts, vol. 100, No. 5, Abst. No. 034408n, Jan. 30, 1984.

*Primary Examiner*—Alan L. Rotman
*Attorney, Agent, or Firm*—Frederick H. Rabin

[57] ABSTRACT

The novel componds of the formula I

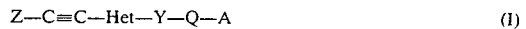

$$Z-C\equiv C-Het-Y-Q-A \qquad (I)$$

are useful selective herbicides for post-emergence application in crops of cereals, rice and maize.

The symbols in the formula I have the following meanings:

Het is a pyridyl radical which is unsubstituted or substituted by one to three radicals R, A is a group $-NR_1R_2$ $R_1$ and $R_2$ independently of one another are each hydrogen, $C_3$–$C_6$-alkenyl, $C_3$–$C_6$-alkynyl, $C_3$–$C_8$-cycloalkyl or Y is oxygen or sulfur, Q is a straight-chain or branched-chain $C_2$–$C_6$-alkylene bridge, R is cyano, $C_1$–$C_4$-alkoxy, di-($C_1$–$C_6$-alkyl)amino or $C_1$–$C_4$ alkyl.

14 Claims, No Drawings

CERTAIN PYRIDYLACETYLENE COMPOUNDS, COMPOSITIONS CONTAINING SAME AND HERBICIDAL METHODS OF USE

The present invention relates to novel heterocyclic acetylene compounds having herbicidal activity, to processes for producing them, to compositions containing them, and to the use thereof for selectively combating weeds in various cultivated crops, for example cereals, maize and rice. The invention relates also to the novel 1,1-dialkyl-3-heterocyclo-propargyl alcohols serving as intermediates, and to the production thereof.

The novel heterocyclic acetylene compounds according to the invention correspond to the general formula I

$$Z-C\equiv C-Het-Y-Q-A \qquad (I)$$

wherein

Het is a 5-6-membered heterocyclic radical which is unsubstituted or substituted by one to three radicals R, and which contains as ring members 1 to 3 hetero atoms from the group comprising nitrogen, oxygen and sulfur, oxygen and sulfur being present at most once per heterocyclic radical, A is a group $-NR_1R_2$ or $-N^{\oplus}HR_1R_2X^{\ominus}$, $R_1$ and $R_2$ independently of one another are each hydrogen, $C_3-C_6$-alkenyl, $C_3-C_6$-alkynyl, $C_3-C_8$-cycloalkyl, or $C_1-C_6$-alkyl which is unsubstituted or substituted by halogen, hydroxyl, $C_1-C_4$-alkoxy, alkoxycarbonyl having at most 5 carbon atoms, cyano or carboxyl, or $R_1$ and $R_2$ together with the nitrogen atom carrying them form a 5- or 6-membered, saturated heterocycle radical having in all at most 2 hetero atoms, which radical can be substituted by $C_1-C_3$-alkyl, $X^{\ominus}$ is an anion, Y is oxygen, sulfur or a radical $-NR_3-$, $R_3$ is hydrogen, $C_3-C_6$-alkenyl, $C_3-C_6$-alkynyl or $C_3-C_8$-cycloalkyl, or $C_1-C_6$-alkyl which is unsubstituted or substituted by hydroxyl, $C_1-C_4$-alkoxy, alkoxycarbonyl having at most 5 carbon atoms, cyano or carboxyl, Q is a straight-chain or branched-chain $C_2-C_6$-alkylene bridge, R is hydrogen, nitro, cyano, trifluoromethyl, $C_1-C_4$-alkoxy, $C_1-C_4$-alkylthio, $-NR_4R_5$, $-CO-NR_6R_7$, $-COOR_8$, $-CO-SR_9$, halogen or $-N_3$, or $C_1-C_4$-alkyl which is unsubstituted or substituted by $C_1-C_4$-alkoxy, hydroxyl, cyano or $-COOR_8$, $R_4$, $R_6$, $R_7$, $R_8$ and $R_9$ independently of one another are each hydrogen or $C_1-C_6$-alkyl, $C_3-C_8$-alkenyl or $C_3-C_8$-alkynyl, $R_5$ is hydrogen, $C_1-C_6$-alkyl, $C_3-C_8$-alkenyl, $C_3-C_8$-alkynyl, $-CO-R_{10}$, $-COO-R_{11}$ or $-CO-NHR_{12}$, and $R_{10}$, $R_{11}$ and $R_{12}$ have the same meaning as $R_3$, and Z is a phenyl, naphthyl or heterocyclic, aromatic group which contains at least one oxygen, sulfur or nitrogen atom, and which is unsubstituted or is substituted by one to three radicals which have the same meaning as that given for R, or are formyl, $-SO_2NR_6R_7$, $-NH-NH_2$, $-NHOH$, $-SO-R_8$, $-SO_2-R_8$, $-N=CH-NR_6R_7$ or $COO^{\ominus}M^{\oplus}$, or $C_2-C_6$-alkenyl which is unsubstituted or substituted by nitro, cyano or $-COOR_8$, $M^{\oplus}$ being a sodium, potassium, calcium or magnesium cation.

Herbicidally effective diarylacetylene compounds have been described recently in the European Patent Application No. 41476, and in Phytochemistry 19, 61 (1980).

In the definition of the compounds of the formula I according to the invention, Het is a 5- or 6-membered heterocyclic radical which can be of aromatic or nonaromatic character.

Examples of aromatic heterocyclic radicals denoted by the symbol Het or Z are: furan, thiophene, triazole, pyridine, oxazole, thiazole, thiadiazole, pyrrole, imidazole, furazan, pyrazole, pyrazine, pyrimidine, pyridazine, symmetrical and asymmetrical triazine or oxadiazole; preferably, however: furan, thiophene, pyridine, pyrimidine, pyrazine, pyridazine, thiazole, thiadiazole, oxadiazole, oxazole, pyrazole, triazole, imidazole and triazine.

Examples of saturated heterocyclic radicals which can be formed by $R_1$ and $R_2$ with the inclusion of the nitrogen atom binding them are: pyrrolidine, imidazolidine, pyrazolidine, piperidine, piperazine, piperimidine, morpholine and thiomorpholine.

Examples of alkyl in the definitions of R and $R_1$ to $R_{12}$ are: methyl, ethyl, n-propyl, i-propyl, the four isomeric butyl groups, as well as the straight-chain or branched-chain pentyl or hexyl groups; preferably, however, the alkyl group is straight-chain and short-chain: it is in particular ethyl or methyl.

Examples of alkoxy in the substituent definitions are: methoxy, ethoxy, n-propyloxy and i-propyloxy, or the four isomeric butyloxy groups, preferably however methoxy or ethoxy.

Examples of alkylthio are: methylthio, ethylthio, n-propylthio or n-butylthio, preferably however methylthio or ethylthio.

Examples of $C_3-C_8$-cycloalkyl are: cyclopropyl, cyclobutyl, cyclopentyl, cyclohexyl, cycloheptyl or cyclooctyl, preferably however cyclopropyl or especially cyclopentyl or cyclohexyl.

Examples of anions $X^{\ominus}$ are the anions of organic and inorganic acids, such as hydrohalic acids, phosphoric acid, sulfuric acid, aliphatic and aromatic sulfonic acids, fatty acids, as well as polyvalent organic acids, such as oxalic acid, malonic acid, succinic acid, adipic acid and citric acid; the anions are preferably however halide anions, such as chloride or bromide.

Examples of alkenyl groups are: allyl, or the isomeric butenyl, pentenyl, hexenyl, heptenyl and octenyl groups, particularly however allyl.

Examples of alkynyl groups are: propargyl, or the isomeric butynyl, pentynyl, hexynyl, heptynyl and octynyl groups, especially however propargyl.

Preferred halogen substituents are chlorine, bromine and iodine.

The alkylene bridge Q is a straight-chain or branched-chain structure, for example: 1,2-ethylene, 1,3-propylene, 1,4-butylene, 1,5-pentylene, 1-methyl-1,2-ethylene, 2-methyl-1,2-ethylene, 1-ethyl-1,2-ethylene, 2-ethyl-1,2-ethylene, 1,2-dimethyl-1,2-ethylene, 1-methyl-1,3-propylene, 2-methyl-1,3-propylene, 3-methyl-1,3-propylene, 1-ethyl-1,3-propylene and 2-methyl-1,3-propylene; the direct chain between the bridge atom Y and the nitrogen atom preferably consists however of 2 or 3 carbon atoms.

Preferred compounds of the formula I are those wherein (a) the heterocyclic radical Het is an unsubstituted or substituted aromatic, 6-membered nitrogen ring, such as pyridine, pyrazine, pyridazine, pyrimidine or triazine;
(b) the heterocyclic radical Het is an unsubstituted or substituted aromatic 5-membered ring, such as furan, thiophene, pyrazole, imidazole, triazole, oxazole, thiazole, thiadiazole or oxadiazole;
(c) Z is unsubstituted or substituted phenyl or thienyl;
(d) the direct alkylene bridge between the bridge atom Y and the nitrogen atom of the group A consists of 2 or 3 carbon atoms;
(e) $R_1$ and $R_2$ are methyl or ethyl, and
(f) the bridge member Y is oxygen.

By combination of the individual features of the groups a-f, there are given further preferred subgroups of compounds of the formula I in which (aa) Het is an unsubstituted or substituted pyridine, pyrazine, pyridazine, pyrimidine or triazine ring, Z is an unsubstituted or substituted phenyl or thienyl ring, $R_1$ and $R_2$ are methyl or ethyl, and Y is oxygen, and the direct alkylene bridge between the bridge atom Y and the nitrogen atom of the group A consists of 2 or 3 carbon atoms; and (bb) Het is an unsubstituted or substituted furan, thiophene, imidazole, triazole, oxazole, thiazole, thiadiazole or oxadiazole ring, Z is an unsubstituted or substituted phenyl or thienyl ring, $R_1$ and $R_2$ are methyl or ethyl, and Y is oxygen, and the direct alkylene bridge between the bridge atom Y and the nitrogen atom of the group A consists of 2 or 3 carbon atoms.

Preferred compounds within the group (aa) are in their turn those in which (ab) Het is an unsubstituted or substituted pyridine or pyrimidine ring, and Z is an unsubstituted or substituted thiophene ring; and (ac) Het is an unsubstituted or substituted pyridine or pyrimidine ring, and Z is an unsubstituted or substituted phenyl ring.

Particular preference among the compounds of the last-mentioned subgroups (ab) and (ac) is given to those compounds in which the alkylene chain between the bridge atom Y and the nitrogen atom of the group A contains 2 carbon atoms.

Preferred individual compounds to be mentioned are:
1-(5-phenylethynyl-pyridyl-2-oxy)-2-diethylaminoethane,
2-(5-phenylethynyl-pyridyl-2-oxy)-1-diethylaminopropane, and
1-[5-(2-thienylethynyl)-pyridyl-2-oxy]-2-diethylaminoethane.

The compounds of the formula I according to the invention can be produced according to the following scheme A. The formulae IV and X are to be understood as being subformulae of the formula I.

Scheme A:

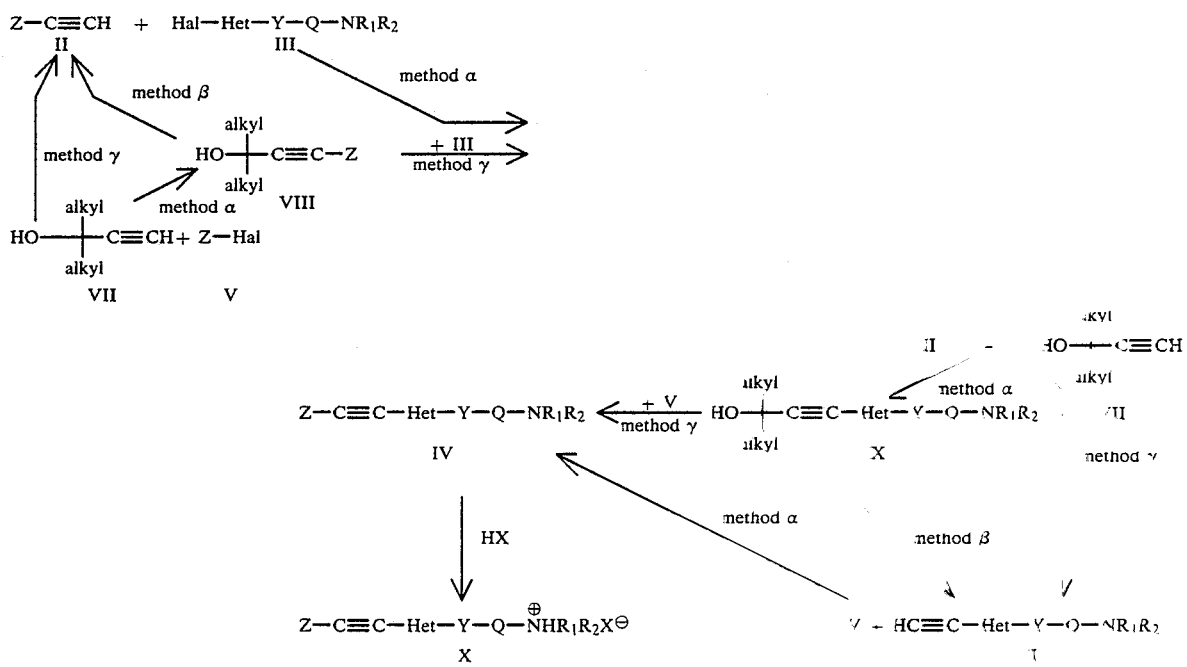

In scheme A, the symbols Het, $R_1$, $R_2$, Q, X, Y and Z have the meanings defined under the formula I. Hal in this case is chlorine, particularly however bromine and iodine.

Method α is a process by which, with the use of metal catalysts, halogenated aromatic radicals, as in the formula III or V, can be bound to terminal acetylene groups, as in the formulae II, VI and VII, under mild reaction conditions and in the presence of an acid-binding agent. Reactions of this type are described in the literature as follows: K. Sonogashira, Y. Tohda and N. Hagihara, Tetrahedron Lett., 50, 4467 (1975); L. Cassar, J. Organomet. Chem., 93, 253 (1975); and H. A. Dieck and F. R. Heck, J. Organomet. Chem., 93, 259 (1975).

This reaction is performed advantageously in organic solvents which are inert to the reactants. Many protic as well as aprotic solvents are suitable, for example: alcohols, ketones, ethers, hydrocarbons, halogenated hydrocarbons, and aromatic solvents, such as: methanol, ethanol, isopropanol, cyclohexanone, acetone, methyl ethyl ketone, diethyl ether, dimethyl ether, tetrahydrofuran, dioxane, cyclohexane, pentane, hexane, heptane, octane, methylene chloride, chloroform, carbon tetrachloride, benzene, toluene or xylene; and also for example dimethyl formamide, dimethyl sulfoxide and acetonitrile, or tertiary amines, such as triethylamine.

Since hydrogen halide is separated in the reaction, the acid-binding agent used can be a base. Suitable for this purpose are strong inorganic bases, such as KOH or NaOH; but organic bases can also be used, for example: triethylamine, diethylamine, pyridine, alcoholates, etc. There are optionally used in the reactions 1-5 equivalents of these bases.

The metal catalysts used are preferably palladium salts or complexes, particularly palladium chloride $PdCl_2$, palladium acetate $Pd(OCOCH_3)_2$, or the palladium dichloro-bis-(triphenylphosphine) complex $Pd Cl_2[P(C_6H_5)_3]_2$, usually with the addition of a copper-(I) salt, especially copper-(I) iodide. The catalysts are used as such, or are absorbed onto a carrier, for example charcoal powder, aluminium oxide, and so forth.

The reaction temperatures are as a rule between 0° and 200° C., chiefly however between room temperature and the boiling temperature of the reaction mixture. The reaction times are in general between ½ and 48 hours.

It is possible using method β to liberate acetylene, as in the formulae II, VI and IX, in the presence of a strong base, such as NaOH, KOH or an alcoholate, from a tertiary ethynyl alcohol, as in the formulae VII, VIII and IX, which can be regarded as a protected terminal acetylene group, with the removal of the keto protecting group. The ketones formed as by-products can be removed by distillation from the reaction mixture during the reaction. Reactions of this type are described in the German Offenlegungsschrift No. 2,905,507 and in the U.S. Pat. No. 4,128,588.

The said reaction is advantageously performed in organic solvents inert to the reactants, for example in solvents such as: alcohols, ethers, ketones, hydrocarbons, halogenated hydrocarbons, aromatic solvents or dimethylformamide, dimethyl sulfoxide or acetonitrile. Examples of such solvents are also: methanol, ethanol, isopropanol, dimethyl ether, diethyl ether, tetrahydrofuran, dioxane, acetone, methyl ethyl ketone, cyclohexanone, cyclohexane, benzene, toluene, xylene, methylene chloride, chloroform or carbon tetrachloride.

The reaction temperature here too is preferably between room temperature and the boiling point of the reaction mixture. The reaction time is in general between ½ and 12 hours.

The method γ consists of a combination of methods α and β, whereby the acetylene to be reacted according to method α is produced in situ by reaction of a strong base with a protected acetylene group of the formulae VII, VIII and IX. The reaction conditions are identical to those of the α method. Essential is however the addition of a strong base, such as NaOH, KOH or the alkali salt of an alcohol.

In the process according to the invention are obtained the compounds of the formula I either by reacting an ethynyl compound of the formula II $$Z-C\equiv CH \qquad (II),$$

in the presence of an acid-binding agent and of a metal catalyst, optionally in an inert gas atmosphere, with a heterocyclic halide of the formula III

Hal—Het—Y—Q—NR$_1$R$_2$ (III), and optionally converting the resulting product into an ammonium salt; or by reacting an aromatic halide of the formula V $$Z-Hal \qquad (V),$$

under the same reaction conditions, with a heterocyclic acetylene derivative of the formula VI $$HC\equiv C-Het-Y-Q-NR_1R_2 \qquad (VI),$$

wherein Het, $R_1$, $R_2$, Y, Q and Z have the meanings defined under the formula I, and Hal is bromine or iodine, and optionally converting the product obtained into an ammonium salt.

By means of a further process according to the invention, the compounds of the formula I are obtained by reacting an aromatic halide of the formula V $$Z-Hal \qquad (V),$$

in the presence of an acid-binding agent and of a metal catalyst, optionally in an inert gas atmosphere, with a propargyl alcohol of the formula VII

and reacting the resulting ethynyl compound of the formula VIII

in the presence of a strong base and of a metal catalyst, optionally in an inert gas atmosphere, with a heterocyclic halide of the formula III Hal—Het—Y—Q—NR$_1$R$_2$ (III), and optionally converting the resulting product into an ammonium salt; or by firstly reacting the heterocyclic halide of the formula III, under the above conditions, with the propargyl alcohol of the formula VII, and then reacting the formed ethynyl compound of the formula IX

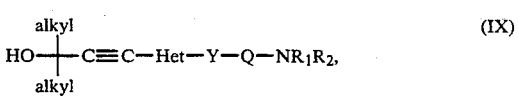

under the above conditions, with the aromatic halide of the formula V, wherein Het, $R_1$, $R_2$, Q and Z have the meanings defined under the formula IV, Hal is bromine or iodine, and alkyl is a $C_1$–$C_4$-alkyl group, and optionally converting the product obtained into an ammonium salt.

The 1,1-dialkyl-3-heterocyclo-proparyl alcohols of the formula IX, which are likewise novel and specially developed as intermediates for the compounds of the formula I, are produced in a manner analogous to that for the first reaction step of the aforementioned process, by reacting a halide of the formula III with a propargyl alcohol of the formula VII.

The compounds of the formula IX likewise form subject matter of the present invention.

In a further process, there are obtained the compounds of the formula X according to the invention

$$Z-C\equiv C-Het-Y-Q-N^{\oplus}HR_1R_2X^{\ominus} \qquad (X)$$

by reacting a compound of the formula IV with an acid HX, and isolating the formed product, in which formula the symbols Het, $R_1$, $R_2$, Q, X, Y and Z have the meanings defined under the formulae I and Ia.

The starting materials of the formulae II, III, V, VI and VII are known, or can be readily produced and/or obtained commercially. Intermediates of the formula VIII are described in the European Patent Application No. 41476.

The novel compounds of the formula I are stable compounds.

The compounds of the subformula IV are relatively easily soluble in the customary organic solvents, but are difficulty soluble in water. They can be readily precipitated by the addition of water to the reaction solution. They can be formulated as liquid herbicidal compositions with the aid of customary solubilisers and/or dispersing agents.

The compounds of the subformula X are readily soluble in water, but are relatively difficultly soluble even in polar organic solvents, such as dimethyl sulfoxide, dimethylformamide or acetonitrile.

The heterocyclic acetylene compounds of the formula I according to the invention influence plant growth, and in the case of post-emergence application they exhibit an excellent selective-herbicidal action against broadleaved weeds which are difficult to control, such as against Galium, Veronica and Viola, but also against Sinapis, Chrysanthemum, and the like, in maize and rice crops, chiefly however in cereal crops. Particularly perennial weeds are effectively combated by translocation of the active substances of the formula I. By translocation is meant the transporting of an active substance within the plant. The active substance can be translocated in the process from the leaves into the roots and conversely, that is, to locations where it can produce the desired effect. Some of the active substances of the formula I are translocatable, that is to say, the roots of the weeds are destroyed by application of the active substances to the leaves.

The compounds of the formula I are used either in an unmodified form or preferably in compositions, together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–(4)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylene-diaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydoxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications: "Mc Cutcheon's Detergents and Emulsifiers Annual" MC Publishing Corp., Ridgewood, N.J., 1979; and Sisley and Wood, "Encyclopedia of Surface Active Agents", Chemical Publishing Co., Inc. New York, 1964.

The agrochemical preparations contain as a rule 0.1 to 99%, especially 0.1 to 95%, of active ingredient of the formula I, 1 to 99% of a solid or liquid additive, and 0 to 25%, particularly 0.1 to 25%, of a tenside.

Preferred formulations are made up in particular as follows (%=percent by weight):

Solutions active ingredient: 5 to 95%, preferably 10 to 80%
solvent: 95 to 5%, preferably 90 to 0%
surface-active agent: 1 to 30%, preferably 2 to 20%.

Emulsifiable concentrates active ingredient: 10 to 50%, preferably 10 to 40%
surface-active agent: 5 to 30%, preferably 10 to 20%
liquid carrier: 20 to 95%, preferably 40 to 80%.

Dusts active ingredient: 0.5 to 10%, preferably 2 to 8%
solid carrier: 99.5 to 90%, preferably 98 to 92%.

Suspension concentrates active ingredient: 5 to 75%, preferably 10 to 50%
water: 94 to 25%, preferably 90 to 30%
surface-active agent: 1 to 40%, preferably 2 to 30%.

Wettable powders active ingredient: 5 to 90%, preferably 10 to 80%, particularly 20 to 60%
surface-active agent: 0.5 to 20%, preferably 1 to 15%
solid carrier: 5 to 90%, preferably 30 to 70%.

Granulates active ingredient: 0.5 to 30%, preferably 3 to 15%
solid carrier: 99.5 to 70%, preferably 97 to 85%.

Whereas commercial products are preferably in the form of concentrated compositions, the compositions employed by the end-user are as a rule diluted. The preparations for application can be diluted down to 0.001% of active ingredient. The applied amounts are as a rule 0.1 to 10 kg, preferably 0.25 to 5 kg of active substance per hectare.

The compositions can also contain additives such as stabilisers, antifoaming agents, viscosity regulators, binders and adhesives, as well as fertilisers or other active substances for obtaining special effects.

In the following Examples, the temperatures are given in degrees Centigrade (°C.), and pressures in millibars (mb).

PRODUCTION EXAMPLES

Example 1

1-(5-Phenylethynyl-pyridyl-2-oxy)-2-diethylaminoethane

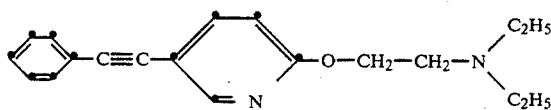

1 g of a palladium complex PdCl$_2$[P(C$_6$H$_5$)$_3$]$_2$ and 500 mg of copper-I-iodide CuJ are added under nitrogen to a solution of 44 g (0.137 mol) of 2-(2-diethylaminoethoxy)-5-iodopyridine and 22 ml (0.192 mol) of phenylacetylene in 350 ml of triethylamine. The reaction mixture warms up to 65° C. and becomes highly viscous. The mixture, after cooling to room temperature, is stirred for 6 hours, and then concentrated by evaporation; the residue is subsequently taken up in ether, and washed four times with ice-water. The yield after the ether has been evaporated off is 35 g (86.5%) of 1-(5-phenylethynyl-pyridyl-2-oxy)-2-diethylaminoethane in the form of wax.

Example 2

2-(5-Phenylethynyl-pyridyl-2-oxy)-1-diethylaminopropane

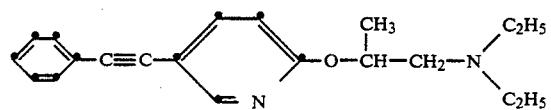

(a) 500 mg of copper-I-iodide and 1 g of a palladium complex PdCl$_2$[P(C$_6$H$_5$)$_3$]$_2$ are added under nitrogen to a solution of 48 g (0.19 mol) of 2-chloro-5-iodopyridine and 20.5 g (0.2 mol) of phenylacetylene in 350 ml of triethylamine. After the initial slightly exothermic reaction, the reaction mixture is stirred for 18 hours at room temperature, then concentrated by evaporation, and subsequently poured into 300 ml of ice-water. The product which has precipitated is filtered off, washed with water and dried to thus obtain 36 g (84%) of 2-chloro-5-phenylethynyl-pyridine, m.p. 70°–72° C.

(b) 750 mg of sodium are added portionwise to a solution of 15 ml (0.102 mol) of 1-diethylamino-2-propanol in 50 ml of xylene, and the solution is heated at 80° C. until the evolution of hydrogen is completed. There are then added to the reaction mixture 6.4 g (0.03 mol) of 2-chloro-5-phenylethynylpyridine, and the mixture is refluxed for 5 hours. 100 ml of ether are added to the cooled reaction mixture, and the whole is washed three times with water, dried, and concentrated by evaporation. The yield after removal of solvent residues under high vacuum (2 mb) is 8.9 g (96.5%) of 2-(5- phenylethynyl-pyridyl-2-oxy)-1-diethylaminopropane, $n_D^{25} = 1.5368$.

Example 3

1-[5-(2-Thienylethynyl)-pyridyl-2-oxy]-2-diethylaminoethane

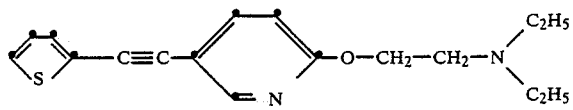

(a) 500 mg of a PdCl$_2$[P(C$_6$H$_5$)$_3$]$_2$ complex and 250 mg of copper-I-iodide are added under nitrogen to a solution of 28 g (0.0875 mol) of 2-(2-diethylaminoethoxy)-5-iodopyridine and 8.4 g (0.1 mol) of 3-methyl-1-butyn-3-ol in 200 ml of triethylamine. The reaction mixture is stirred for 18 hours at room temperature, and is then concentrated by evaporation; the residue is taken up in ether, washed three times with ice-water, dried, and concentrated by evaporation. The yield is thus 19 g (96%) of 2-(2-diethylamino-ethoxy)-5-(3-methyl-3-hydroxy-1-butynyl)-pyridine, which can be further used without purification.

(b) A mixture of 7.5 g (0.0332 mol) of crude 2-(2-diethylamino-ethoxy)-5-(3-methyl-3-hydroxy-1-butynyl)-pyridine, 6.3 g (0.03 mol) of 2-iodothiophene, 3 g of powdered potassium hydroxide, 500 mg of PdCl$_2$[P(C$_6$H$_5$)$_3$]$_2$ complex, 150 mg of copper-1-iodide and 100 ml of triethylamine are refluxed for 18 hours. The mixture is cooled, and concentrated by evaporation; it is then taken up in ethyl acetate, washed three times with ice-water, dried, and concentrated by evaporation. By filtration through a short silica gel column with chloroform/methanol (10:1), there is obtained, after removal of the solvent, a yield of 4.4 g (44%) of 1-[5-(2-thienylethynyl)-pyridyl-2-oxy]-2-diethylaminoethane, $n_D^{25}$: 1.6176.

The compounds obtained from the Examples and those which can be produced in an analogous manner are listed in the Tables which follow.

TABLE 1

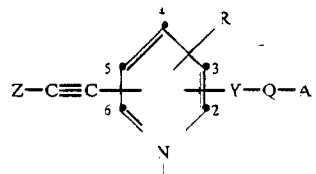

| No. | Z— | Position of —C≡C—Z | —Y—Q—A | Position of —Y—Q—A | R | Physical data |
|---|---|---|---|---|---|---|
| 1 | C$_6$H$_5$— | 5 | —OCH$_2$—CH$_2$—N(C$_2$H$_5$)$_2$ | | H | wax |
| 2 | C$_6$H$_5$— | 5 | —OCH(CH$_3$)—CH$_2$—N(C$_2$H$_5$)$_2$ | | H | $n_D^{25}$ 1.5368 |
| 3 | C$_6$H$_5$— | 5 | —OCH$_2$—CH(CH$_3$)—N(C$_2$H$_5$)$_2$ | | H | $n_D^{25}$ 1.6048 |
| 4 | 2-thienyl | 5 | —OCH$_2$—CH$_2$—N(C$_2$H$_5$)$_2$ | | H | $n_D^{25}$ 1.6176 |
| 5 | 4-F—C$_6$H$_4$— | 5 | —OCH$_2$—CH$_2$—N(C$_2$H$_5$)$_2$ | | H | $n_D^{25}$ 1.5852 |
| 6 | 4-OCH$_3$—C$_6$H$_4$— | 5 | —OCH$_2$—CH$_2$—N(C$_2$H$_5$)$_2$ | | H | resin |
| 7 | C$_6$H$_5$— | 2 | —OCH$_2$—CH$_2$—N(C$_2$H$_5$)$_2$ | | H | resin |
| 8 | C$_6$H$_5$— | 6 | —OCH$_2$—CH$_2$—N(CH$_3$)C$_2$H$_5$ | | H | |
| 9 | C$_6$H$_5$— | 2 | —OCH$_2$—CH$_2$—N(C$_3$H$_7$)$_2$ | | H | |
| 10 | 4-CN—C$_6$H$_4$— | 2 | —OCH$_2$—CH$_2$—N⟨ ⟩ (morpholine) | | H | |
| 11 | C$_6$H$_5$— | 5 | —OCH$_2$—CH$_2$—N(CH$_3$)$_2$ | | CN | |
| 12 | C$_6$H$_5$— | 5 | —OCH$_2$—CH$_2$—N(CH$_3$)$_2$ | | Cl | |
| 13 | C$_6$H$_5$— | 2 | —OCH$_2$—CH$_2$—N(CH$_3$)$_2$ | | Cl | |
| 14 | C$_6$H$_5$— | 5 | —SCH$_2$—CH$_2$—N(C$_2$H$_5$)$_2$ | | H | $n_D^{25}$ 1.6333 |
| 15 | 2-thienyl— | 5 | —SCH$_2$—CH$_2$—N(C$_2$H$_5$)$_2$ | | H | |
| 16 | 4-F—C$_6$H$_4$— | 5 | —N(CH$_3$)—(CH$_2$)$_2$—N(CH$_3$)C$_2$H$_5$ | | H | |
| 17 | 3-thienyl | 5 | —OCH$_2$—CH$_2$—N(C$_2$H$_5$)$_2$ | | H | |
| 18 | 3-F—C$_6$H$_4$— | 5 | —OCH$_2$—CH$_2$—N(C$_2$H$_5$)$_2$ | | H | |
| 19 | 4-pyridyl— | 5 | —OCH$_2$—CH$_2$—N(C$_2$H$_5$)$_2$ | | H | |
| 20 | 4-OCH$_3$—C$_6$H$_4$— | 5 | —SCH$_2$—CH$_2$—N(C$_2$H$_5$)$_2$ | | H | |
| 21 | 2-thienyl— | 5 | —SCH(CH$_3$)—CH$_2$—N(CH$_3$)$_2$ | | H | |
| 22 | 4-F—C$_6$H$_4$— | 5 | —SCH$_2$—CH$_2$—N(C$_2$H$_5$)$_2$ | | H | |
| 23 | 4-OH—C$_6$H$_4$— | 5 | —OCH$_2$—CH$_2$—N(C$_2$H$_5$)$_2$ | | H | |

TABLE 2

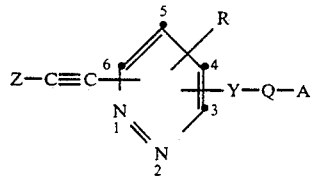

| No. | Z— | Position of —C≡C—Z | —Y—Q—A | Position of —Y—Q—A | R | Physical data |
|---|---|---|---|---|---|---|
| 101 | $C_6H_5$— | 6 | —$OCH_2$—$CH_2$—$N(C_2H_5)_2$ | 3 | H | m.p. 69–71° C. |
| 102 | $C_6H_5$— | 6 | —$OCH_2$—$CH_2$—$N(CH_3)_2$ | 4 | H | |
| 103 | $C_6H_5$— | 6 | —$OCH(CH_3)$—$CH_2$—$N(CH_3)_2$ | 3 | H | |
| 104 | 4-F—$C_6H_4$— | 6 | —$OCH_2$—$CH(CH_3)$—$N(CH_3)_2$ | 3 | H | |
| 105 | 4-$OCH_3$—$C_6H_4$— | 6 | —O—$(CH_2)_3$—$N(C_2H_5)_2$ | 3 | H | |
| 106 | 2-thienyl— | 6 | —$OCH_2$—$CH_2$—$N(CH_3)C_2H_5$ | 4 | H | |
| 107 | $C_6H_5$— | 6 | —$N(C_3H_7)$—$CH_2$—$CH_2$—$N(CH_3)_2$ | 3 | H | |
| 108 | 3-$OCH_3$—5-$OCH_3$—$C_6H_3$— | 6 | —$SCH_2$—$CH_2$—$N(CH_3)_2$ | 4 | H | |
| 109 | $C_6H_5$— | 6 | —$OCH_2$—$CH_2$—$N(C_2H_5)_2$ | 4 | 4-Cl | |

TABLE 3

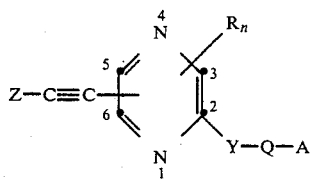

| No. | Z— | Position of —C≡C—Z | —Y—Q—A | $R_n$ |
|---|---|---|---|---|
| 151 | $C_6H_5$— | 6 | —$OCH_2$—$CH_2$—$N(C_2H_5)_2$ | H |
| 152 | $C_6H_5$— | 5 | —$OCH_2$—$CH_2$—$N(C_2H_5)_2$ | H |
| 153 | $C_6H_5$— | 6 | —$OCH_2$—$CH_2$—$N(C_2H_5)_2$ | 3-Cl, 5-Cl |
| 154 | $C_6H_5$— | 5 | —$OCH_2$—$CH_2$—$N(C_2H_5)_2$ | 3-Cl, 6-Cl |
| 155 | 4-F—$C_6H_4$— | 6 | —$OCH_2$—$CH_2$—$N(CH_3)C_3H_7$ | H |
| 156 | 4-$OCH_3$—$C_6H_4$— | 5 | —$OCH(CH_3)$—$CH_2$—$N(CH_3)_2$ | H |
| 157 | 2-thienyl- | 5 | —O—$(CH_2)_3$—$N(CH_3)_2$ | H |
| 158 | 2-thienyl- | 5 | —$SCH_2$—$CH_2$—$N(CH_3)_2$ | H |
| 159 | 2-Cl-5-pyridyl- | 5 | —$N(CH_3)$—$CH_2$—$CH_2$—$N(CH_3)_2$ | H |
| 160 | 3-thienyl- | 5 | —$OCH_2$—$CH_2$—$N(C_2H_5)_2$ | H |

TABLE 4

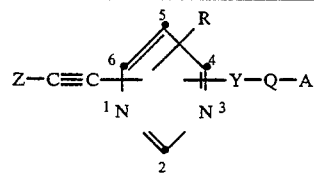

| No. | Z— | Position of —C≡C—Z | —Y—Q—A | Position of —Y—Q—A | R | Physical data |
|---|---|---|---|---|---|---|
| 201 | $C_6H_5$— | 2 | —$OCH_2$—$CH_2$—$N(C_2H_5)_2$ | 5 | H | |
| 202 | $C_6H_5$— | 2 | —$OCH(CH_3)$—$CH_2$—$N(CH_3)_2$ | 5 | H | |
| 203 | $C_6H_5$— | 2 | —$OCH_2$—$CH(CH_3)$—$N(CH_3)_2$ | 5 | H | |
| 204 | $C_6H_5$— | 2 | —O—$(CH_2)_3$—$N(C_2H_5)_2$ | 5 | H | |
| 205 | $C_6H_5$— | 2 | —$OCH_2$—$CH_2$—$N(CH_3)C_2H_5$ | 5 | H | |
| 206 | 2-thienyl- | 2 | —$OCH_2$—$CH_2$—$N(C_2H_5)_2$ | 5 | H | |
| 207 | 2-thienyl- | 2 | —$OCH(CH_3)$—$CH_2$—$N(CH_3)_2$ | 5 | H | |
| 208 | 2-thienyl- | 2 | —$OCH_2$—$CH(CH_3)$—$N(CH_3)_2$ | 5 | H | |
| 209 | 2-thienyl- | 2 | —$OCH_2$—$CH_2$—$N(CH_3)C_2H_5$ | 5 | H | |
| 210 | 4-F—$C_6H_4$— | 2 | —$OCH_2$—$CH_2$—$N(C_2H_5)_2$ | 5 | H | |
| 211 | 4-F—$C_6H_4$— | 2 | —$OCH(CH_3)$—$CH_2$—$N(CH_3)_2$ | 5 | H | |
| 212 | 4-F—$C_6H_4$— | 2 | —$OCH_2$—$CH(CH_3)$—$N(CH_3)_2$ | 5 | H | |
| 213 | 4-F—$C_6H_4$— | 2 | —$OCH_2$—$CH_2$—$N(CH_3)C_2H_5$ | 5 | H | |
| 214 | 4-$OCH_3$—$C_6H_4$— | 2 | —$OCH_2$—$CH_2$—$N(C_2H_5)_2$ | 5 | H | |
| 215 | 4-$OCH_3$—$C_6H_4$— | 2 | —$OCH(CH_3)$—$CH_2$—$N(CH_3)_2$ | 5 | H | |
| 216 | 4-$OCH_3$—$C_6H_4$— | 2 | —$OCH_2$—$CH(CH_3)$—$N(CH_3)_2$ | 5 | H | |
| 217 | 4-$OCH_3$—$C_6H_4$— | 2 | —$OCH_2$—$CH_2$—$N(CH_3)C_2H_5$ | 5 | H | |
| 218 | $C_6H_5$— | 5 | —$OCH_2$—$CH_2$—$N(C_2H_5)_2$ | 2 | H | oil |
| 219 | $C_6H_5$— | 5 | —$OCH(CH_3)$—$CH_2$—$N(CH_3)_2$ | 2 | H | |

TABLE 4-continued $$Z-C\equiv C-\overset{6}{\underset{N^1}{C}}=\overset{5}{\underset{\underset{2}{N^3}}{C}}-\overset{R}{\underset{4}{C}}-Y-Q-A$$

| No. | Z— | Position of —C≡C—Z | —Y—Q—A | Position of —Y—Q—A | R | Physical data |
|---|---|---|---|---|---|---|
| 220 | C₆H₅— | 5 | —OCH₂—CH(CH₃)—N(CH₃)₂ | 2 | H | |
| 221 | C₆H₅— | 5 | —OCH₂—CH₂—N(CH₃)C₂H₅ | 2 | H | |
| 222 | C₆H₅— | 5 | —O—(CH₂)₃—N(C₂H₅)₂ | 2 | H | |
| 223 | 2-thienyl— | 5 | —OCH₂—CH₂—N(C₂H₅)₂ | 2 | H | m. p. 56° C. |
| 224 | 2-thienyl— | 5 | —OCH(CH₃)—CH₂—N(CH₃)₂ | 2 | H | |
| 225 | 2-thienyl— | 5 | —OCH₂—CH(CH₃)—N(CH₃)₂ | 2 | H | |
| 226 | 2-thienyl— | 5 | —OCH₂—CH₂—N(CH₃)C₂H₅ | 2 | H | |
| 227 | 4-F—C₆H₄— | 5 | —OCH₂—CH₂—N(C₂H₅)₂ | 2 | H | m. p. 79–82° C. |
| 228 | 4-F—C₆H₄— | 5 | —OCH(CH₃)—CH₂—N(CH₃)₂ | 2 | H | |
| 229 | 4-F—C₆H₄— | 5 | —OCH₂—CH(CH₃—N(CH₃)₂ | 2 | H | |
| 230 | 4-F—C₆H₄— | 5 | —OCH₂—CH₂—N(CH₃)C₂H₅ | 2 | H | |
| 231 | 4-OCH₃—C₆H₄— | 5 | —OCH₂—CH₂—N(C₂H₅)₂ | 2 | H | |
| 232 | 4-OCH₃—C₆H₄— | 5 | —OCH(CH₃)—CH₂—N(CH₃)₂ | 2 | H | |
| 233 | 4-OCH₃—C₆H₄— | 5 | —OCH₂—CH(CH₃)—N(CH₃)₂ | 2 | H | |
| 234 | 4-OCH₃—C₆H₄— | 5 | —OCH₂—CH₂—N(CH₃)C₂H₅ | 2 | H | |
| 235 | C₆H₅— | 2 | —OCH₂—CH₂—N(C₂H₅)₂ | 4 | H | |
| 236 | C₆H₅— | 2 | —OCH₂—CH₂—N(C₂H₅)₂ | 4 | 6-CH₃ | |
| 237 | C₆H₅— | 2 | —OCH₂—CH₂—N(C₂H₅)₂ | 4 | 6-F | |
| 238 | C₆H₅— | 2 | —OCH₂—CH₂—N(C₂H₅)₂ | 4 | 6-Cl | |
| 239 | C₆H₅— | 2 | —OCH(CH₃)—CH₂—N(CH₃)₂ | 4 | H | |
| 240 | C₆H₅— | 2 | —OCH(CH₃)—CH₂—N(CH₃)₂ | 4 | 6-F | |
| 241 | C₆H₅— | 2 | —OCH(CH₃)—CH₂—N(CH₃)₂ | 4 | 6-Cl | |
| 242 | C₆H₅— | 2 | —OCH₂—CH₂—N(CH₃)C₂H₅ | 4 | 6-F | |
| 243 | C₆H₅— | 2 | —OCH(CH₃)—CH₂—N(CH₃)₂ | 4 | H | |
| 244 | C₆H₅— | 2 | —OCH₂—CH(CH₃)—N(CH₃)₂ | 4 | 6-CH₃ | |
| 245 | C₆H₅— | 2 | —OCH₂—CH(CH₃)—N(CH₃)₂ | 4 | 6-Cl | |
| 246 | C₆H₅— | 2 | —OCH₂—CH₂—N(CH₃)C₂H₅ | 4 | H | |
| 247 | C₆H₅— | 2 | —O—(CH₂)₃—N(C₂H₅)₂ | 4 | H | |
| 248 | 2-thienyl- | 2 | —OCH₂—CH₂—N(C₂H₅)₂ | 4 | H | |
| 249 | 2-thienyl- | 2 | —OCH₂—CH₂—N(C₂H₅)₂ | 4 | 6-CH₃ | |
| 250 | 2-thienyl- | 2 | —OCH₂—CH₂—N(C₂H₅)₂ | 4 | 6-Cl | |
| 251 | 2-thienyl- | 2 | —OCH₂—CH₂—N(C₂H₅)₂ | 4 | 6-F | |
| 252 | 2-thienyl- | 2 | —OCH(CH₃)—CH₂—N(CH₃)₂ | 4 | H | |
| 253 | 2-thienyl- | 2 | —OCH(CH₃)—CH₂—N(CH₃)₂ | 4 | 6-CH₃ | |
| 254 | 2-thienyl- | 2 | —OCH(CH₃)—CH₂—N(CH₃)₂ | 4 | 6-Cl | |
| 255 | 2-Thienyl- | 2 | —OCH₂—CH(CH₃)—N(CH₃)₂ | 4 | H | |
| 256 | 2-Thienyl- | 2 | —OCH₂—CH(CH₃)—N(CH₃)₂ | 4 | 6-F | |
| 257 | 2-Thienyl- | 2 | —OCH₂—CH(CH₃)—N(CH₃)₂ | 4 | 6-Cl | |
| 258 | 2-Thienyl- | 2 | —OCH₂—CH₂—N(CH₃)C₂H₅ | 4 | H | |
| 259 | 4-F—C₆H₄— | 2 | —OCH₂—CH₂—N(C₂H₅)₂ | 4 | H | |
| 260 | 4-F—C₆H₄— | 2 | —OCH₂—CH₂—N(C₂H₅)₂ | 4 | H | |
| 261 | 4-F—C₆H₄— | 2 | —OCH(CH₃)—CH₂—N(CH₃)₂ | 4 | H | |
| 262 | 4-OCH₃—C₆H₄— | 2 | —OCH₂—CH₂—N(C₂H₅)₂ | 4 | H | |
| 263 | 4-OCH₃—C₆H₄— | 2 | —OCH₂—CH₂—N(C₂H₅)₂ | 4 | H | |
| 264 | 4-OCH₃—C₆H₄— | 2 | —OCH(CH₃)—CH₂—N(CH₃)₂ | 4 | 6-F | |
| 265 | 4-OCH₃—C₆H₄— | 2 | —OCH₂—CH(CH₃)—N(CH₃)₂ | 4 | H | |
| 266 | 3-thienyl- | 2 | —OCH₂—CH₂—N(C₂H₅)₂ | 4 | H | |
| 267 | 3-thienyl- | 2 | —OCH₂—CH₂—N(C₂H₅)₂ | 4 | 6-F | |
| 268 | 3-thienyl- | 2 | —OCH(CH₃)—CH₂—N(CH₃)₂ | 4 | H | |
| 269 | 3-thienyl- | 2 | —O—(CH₂)₃—N(C₂H₅)₂ | 4 | H | |
| 270 | 3-thienyl- | 2 | —OCH₂—CH(CH₃)—N(CH₃)₂ | 4 | H | |
| 271 | 3-thienyl- | 2 | —OCH₂—CH₂—N(C₂H₅)₂ | 4 | 6-CH₃ | |
| 272 | 3-thienyl- | 2 | —OCH₂—CH₂—N(C₂H₅)₂ | 4 | 6-Cl | |
| 273 | 3-thienyl- | 2 | —OCH₂—CH₂—N(C₂H₅)₂ | 5 | H | |
| 274 | 3-thienyl- | 2 | —OCH(CH₃)—CH₂—N(CH₃)₂ | 5 | H | |
| 275 | 3-thienyl- | 2 | —OCH₂—CH(CH₃)—N(CH₃)₂ | 5 | H | |
| 276 | 3-thienyl- | 2 | —O—(CH₂)₃—N(C₂H₅)₂ | 5 | H | |
| 277 | 3-thienyl- | 2 | —OCH₂—CH₂—N(CH₃)C₂H₅ | 5 | H | |
| 278 | 3-thienyl- | 5 | —OCH₂—CH₂—N(C₂H₅)₂ | 2 | H | |
| 279 | 3-thienyl- | 5 | —OCH(CH₃)—CH₂—N(CH₃)₂ | 2 | H | |
| 280 | 3-thienyl- | 5 | —OCH₂—CH(CH₃)—N(CH₃)₂ | 2 | H | |
| 281 | 3-thienyl- | 5 | —O—(CH₂)₃—N(C₂H₅)₂ | 2 | H | |
| 282 | 3-thienyl- | 5 | —OCH₂—CH₂—N(CH₃)C₂H₅ | 2 | H | |
| 283 | C₆H₅— | 4 | —OCH₂—CH₂—N(C₂H₅)₂ | 2 | H | oil |
| 284 | C₆H₅— | 4 | —OCH₂—CH₂—N(C₂H₅)₂ | 2 | 6-CH₃ | |
| 285 | C₆H₅ | 4 | —OCH₂—CH₂—N(C₂H₅)₂ | 2 | 6-Cl | $n_D^{25}$ 1.5940 |
| 286 | C₆H₅— | 4 | —OCH₂—CH₂—N(C₂H₅)₂ | 2 | 6-F | |
| 287 | C₆H₅— | 4 | —OCH(CH₃)—CH₂—N(CH₃)₂ | 2 | H | |
| 288 | C₆H₅— | 4 | —OCH(CH₃)—CH₂—N(CH₃)₂ | 2 | 6-CH₃ | |
| 289 | C₆H₅— | 4 | —OCH(CH₃)—CH₂—N(CH₃)₂ | 2 | 6-Cl | |
| 290 | C₆H₅— | 4 | —OCH(CH₃)—CH₂—N(CH₃)₂ | 2 | 6-F | |

TABLE 4-continued

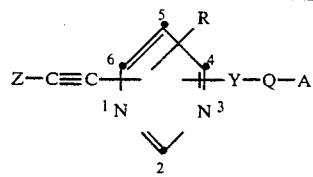

| No. | Z— | Position of —C≡C—Z | —Y—Q—A | Position of —Y—Q—A | R | Physical data |
|---|---|---|---|---|---|---|
| 291 | $C_6H_5$— | 4 | —$OCH_2$—$CH(CH_3)$—$N(CH_3)_2$ | 2 | H | |
| 292 | $C_2H_5$— | 4 | —$OCH_2$—$CH(CH_3)$—$N(CH_3)_2$ | 2 | 6-$CH_3$ | |
| 293 | $C_6H_5$— | 4 | —$OCH_2$—$CH(CH_3)$—$N(CH_3)_2$ | 2 | 6-Cl | |
| 294 | $C_6H_5$— | 4 | —$OCH_2$—$CH(CH_3)$—$N(CH_3)_2$ | 2 | 6-F | |
| 295 | $C_6H_5$— | 4 | —O—$(CH_2)_3$—$N(C_2H_5)_2$ | 2 | H | |
| 296 | $C_6H_5$— | 4 | —$OCH_2$—$CH_2$—$N(CH_3)C_2H_5$ | 2 | H | |
| 297 | 2-thienyl- | 4 | —$OCH_2$—$CH_2$—$N(C_2H_5)_2$ | 2 | H | |
| 298 | 2-thienyl- | 4 | —$OCH_2$—$CH_2$—$N(C_2H_5)_2$ | 2 | 6-$CH_3$ | |
| 299 | 2-thienyl- | 4 | —$OCH_2$—$CH_2$—$N(C_2H_5)_2$ | 2 | 6-Cl | |
| 300 | 2-thienyl- | 4 | —$OCH_2$—$CH_2$—$N(C_2H_5)_2$ | 2 | 6-F | |
| 301 | 2-thienyl- | 4 | —$OCH(CH_3)$—$CH_2$—$N(CH_3)_2$ | 2 | H | |
| 302 | 2-thienyl- | 4 | —$OCH(CH_3)$—$CH_2$—$N(CH_3)_2$ | 2 | 6-Cl | |
| 303 | 2-thienyl- | 4 | —$OCH(CH_3)$—$CH_2$—$N(CH_3)_2$ | 2 | 6-F | |
| 304 | 2-thienyl- | 4 | —$OCH(CH_3)$—$CH_2N(CH_3)_2$ | 2 | 6-$CH_3$ | |
| 305 | 2-thienyl- | 4 | —$OCH_2$—$CH(CH_3)$—$N(CH_3)_2$ | 2 | 6-$CH_3$ | |
| 306 | 2-thienyl- | 4 | —$OCH_2$—$CH(CH_3)$—$N(CH_3)_2$ | 2 | 6-$CH_3$ | |
| 307 | 2-thienyl- | 4 | —$OCH_2$—$CH(CH_3)$—$N(CH_3)_2$ | 2 | 6-Cl | |
| 308 | 2-thienyl- | 4 | —$OCH_2$—$CH(CH_3)$—$N(CH_3)_2$ | 2 | 6-F | |
| 309 | 2-thienyl- | 4 | —O—$(CH_2)_3$—$N(C_2H_5)_2$ | 2 | H | |
| 310 | 2-thienyl- | 4 | —O—$(CH_2)_3$—$N(CH_3)_2$ | 2 | H | |
| 311 | 2-thienyl- | 4 | —$OCH_2$—$CH_2$—$N(CH_3)C_2H_5$ | 2 | H | |
| 312 | 4-F—$C_6H_4$— | 4 | —$OCH_2$—$CH_2$—$N(C_2H_5)_2$ | 2 | H | |
| 313 | 4-F—$C_6H_4$— | 4 | —$OCH_2$—$CH_2$—$N(C_2H_5)_2$ | 2 | 6-$CH_3$ | |
| 314 | 4-F—$C_6H_4$ | 4 | —$OCH_2$—$CH_2$—$N(C_2H_5)_2$ | 2 | 6-Cl | |
| 315 | 4-F—$C_6H_4$— | 4 | —$OCH_2$—$CH_2$—$N(C_2H_5)_2$ | 2 | 6-F | |
| 316 | 4-F—$C_6H_4$— | 4 | —$OCH(CH_3)$—$CH_2$—$N(CH_3)_2$ | 2 | H | |
| 317 | 4-F—$C_6H_4$— | 4 | —$OCH(CH_3)$—$CH_2$—$N(CH_3)_2$ | 2 | 6-$CH_3$ | |
| 318 | 4-F—$C_6H_4$— | 4 | —$OCH(CH_3)$—$CH_2$—$N(CH_3)_2$ | 2 | 6-Cl | |
| 319 | 4-F—$C_6H_4$— | 4 | —$OCH(CH_3)$—$CH_2$—$N(CH_3)_2$ | 2 | 6-F | |
| 320 | 4-F—$C_6H_4$— | 4 | —$OCH_2$—$CH(CH_3)$—$N(CH_3)_2$ | 2 | H | |
| 321 | 4-F—$C_6H_4$— | 4 | —$OCH_2$—$CH(CH_3)$—$N(CH_3)_2$ | 2 | 6-$CH_3$ | |
| 322 | 4-F—$C_6H_4$— | 4 | —$OCH_2$—$CH(CH_3)$—$N(CH_3)_2$ | 2 | 6-F | |
| 323 | 4-F—$C_6H_4$— | 4 | —O—$(CH_2)_3$—$N(C_2H_5)_2$ | 2 | H | |
| 324 | 4-F—$C_6H_4$— | 4 | —O—$(CH_2)_3$—$N(CH_3)_2$ | 2 | H | |
| 325 | 4-F—$C_6H_4$— | 4 | —$OCH_2$—$CH_2$—$N(CH_3)C_2H_5$ | 2 | H | |
| 326 | 4-$OCH_3$—$C_6H_4$— | 4 | —$OCH_2$—$CH_2$—$N(C_2H_5)_2$ | 2 | H | |
| 327 | 4-$OCH_3$—$C_6H_4$— | 4 | —$OCH_2$—$CH_2$—$N(C_2H_5)_2$ | 2 | 6-$CH_3$ | |
| 328 | 4-$OCH_3$—$C_6H_4$— | 4 | —$OCH_2$—$CH_2$—$N(C_2H_5)_2$ | 2 | 6-Cl | |
| 329 | 4-$OCH_3$—$C_6H_4$— | 4 | —$OCH_2$—$CH_2$—$N(C_2H_5)_2$ | 2 | 6F | |
| 330 | 4-$OCH_3$—$C_6H_4$— | 4 | —$OCH(CH_3)$—$CH_2$—$N(CH_3)_2$ | 2 | H | |
| 331 | 4-$OCH_3$—$C_6H_4$— | 4 | —$OCH(CH_3)$—$CH_2$—$N(CH_3)_2$ | 2 | 6-$CH_3$ | |
| 332 | 4-$OCH_3$—$C_6H_4$— | 4 | —$OCH(CH_3)$—$CH_2$—$N(CH_3)_2$ | 2 | 6-Cl | |
| 333 | 4-$OCH_3$—$C_6H_4$— | 4 | —$OCH(CH_3)$—$CH_2$—$N(CH_3)_2$ | 2 | 6-F | |
| 334 | 4-$OCH_3$—$C_6H_4$— | 4 | —$OCH_2$—$CH(CH_3)$—$N(CH_3)_2$ | 2 | H | |
| 335 | 4-$OCH_3$—$C_6H_4$ | 4 | —$OCH_2$—$CH(CH_3)$—$N(CH_3)_2$ | 2 | 6-$CH_3$ | |
| 336 | 4-$OCH_3$—$C_6H_4$— | 4 | —$OCH_2$—$CH(CH_3)$—$N(CH_3)_2$ | 2 | 6-Cl | |
| 337 | 4-$OCH_3$—$C_6H_4$— | 4 | —$OCH_2$—$CH(CH_3)$—$N(CH_3)_2$ | 2 | 6-F | |
| 338 | 4-$OCH_3$—$C_6H_4$— | 4 | —O—$(CH_2)_3$—$N(C_2H_5)_2$ | 2 | H | |
| 339 | 4-$OCH_3$—$C_6H_4$— | 4 | —O—$(CH_2)_3$—$N(CH_3)_2$ | 2 | H | |
| 340 | 4-$OCH_3$—$C_6H_4$— | 4 | —$OCH_2$—$CH_2$—$N(CH_3)C_2H_5$ | 2 | H | |
| 341 | $C_6H_5$— | 4 | —$OCH_2$—$CH_2$—$N(C_2H_5)_2$ | 6 | H | |
| 342 | $C_6H_5$— | 4 | —$OCH(CH_3)$—$CH_2$—$N(CH_3)_2$ | 6 | H | |
| 343 | $C_6H_5$— | 4 | —$OCH_2$—$CH(CH_3)$—$N(CH_3)_2$ | 6 | H | |
| 344 | $C_6H_5$— | 4 | —O—$(CH_2)_3$—$N(C_2H_5)_2$ | 6 | H | |
| 345 | $C_6H_5$— | 4 | —O—$(CH_2)_3$—$N(CH_3)_2$ | 6 | H | |
| 346 | 2-thienyl- | 4 | —$OCH_2$—$CH_2$—$N(C_2H_5)_2$ | 6 | H | |
| 347 | 2-thienyl- | 4 | —$OCH_2$—$CH(CH_3)$—$N(CH_3)_2$ | 6 | H | |
| 348 | 2-thienyl- | 4 | —$OCH_2$—$CH(CH_3)$—$N(CH_3)_2$ | 6 | H | |
| 349 | 3-thienyl- | 4 | —$OCH_2$—$CH_2$—$N(C_2H_5)_2$ | 6 | H | |
| 350 | 3-thienyl- | 4 | —$OCH(CH_3)$—$CH_2$—$N(CH_3)_2$ | 6 | H | |
| 351 | 3-thienyl- | 4 | —$OCH_2$—$CH(CH_3)$—$N(CH_3)_2$ | 6 | H | |
| 352 | 4-F—$C_6H_4$— | 4 | —$OCH_2$—$CH_2$—$N(C_2H_5)_2$ | 6 | H | |
| 353 | 4-F—$C_6H_4$— | 4 | —$OCH(CH_3)$—$CH_2$—$N(CH_3)_2$ | 6 | H | |
| 354 | 4-F—$C_6H_4$— | 4 | —$OCH_2$—$CH(CH_3)$—$N(CH_3)_2$ | 6 | H | |
| 355 | 4-$OCH_3$—$C_6H_4$— | 4 | —$OCH_2$—$CH_2$—$N(C_2H_5)_2$ | 6 | H | |
| 356 | 4-$OCH_3$—$C_6H_4$— | 4 | —$OCH_2$—$CH(CH_3)$—$N(CH_3)_2$ | 6 | H | |
| 357 | 4-$OCH_3$—$C_6H_4$— | 4 | —$OCH_2$—$CH(CH_3)$—$N(CH_3)_2$ | 6 | H | |
| 358 | 4-pyridyl- | 5 | —$OCH_2$—$CH_2$—$N(C_2H_5)_2$ | 2 | H | |
| 359 | 4-$CH_3$—$C_6H_4$— | 5 | —$OCH_2$—$CH_2$—$N(C_2H_5)_2$ | 2 | H | |
| 360 | 3-F—$C_6H_4$— | 5 | —$OCH_2$—$CH_2$—$N(C_2H_5)_2$ | 2 | H | |
| 361 | 3-F—$C_6H_4$— | 5 | —$OCH(CH_3)$—$CH_2$—$N(CH_3)_2$ | 2 | H | |

TABLE 4-continued

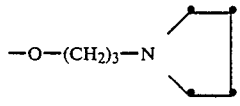

| No. | Z— | Position of —C≡C—Z | —Y—Q—A | Position of —Y—Q—A | R | Physical data |
|---|---|---|---|---|---|---|
| 362 | 3-F—C$_6$H$_4$— | 5 | —OCH$_2$—CH(CH$_3$)—N(CH$_3$)$_2$ | 2 | H | |
| 363 | 3-OCH$_3$—C$_6$H$_4$— | 5 | —OCH$_2$—CH$_2$—N(C$_2$H$_5$)$_2$ | 2 | H | |
| 364 | 3-OCH$_3$—C$_6$H$_4$— | 5 | —OCH(CH$_3$)—CH$_2$—N(CH$_3$)$_2$ | 2 | H | |
| 365 | 3-OCH$_3$—C$_6$H$_4$— | 5 | —OCH$_2$—CH(CH$_3$)—N(CH$_3$)$_2$ | 2 | H | |
| 366 | 4-OCF$_3$—C$_6$H$_4$— | 5 | —OCH$_2$—CH$_2$—N(C$_2$H$_5$)$_2$ | 2 | H | |
| 367 | 4-OH—C$_6$H$_4$— | 5 | —OCH$_2$—CH$_2$—N(C$_2$H$_5$)$_2$ | 2 | H | |
| 368 | 4-Cl—C$_6$H$_4$— | 5 | —OCH$_2$—CH$_2$—N(C$_2$H$_5$)$_2$ | 2 | H | |
| 369 | 4-NO$_2$—C$_6$H$_4$— | 5 | —OCH$_2$—CH$_2$—N(C$_2$H$_5$)$_2$ | 2 | H | |
| 370 | 4-CF$_3$—C$_6$H$_4$— | 5 | —OCH$_2$—CH$_2$—N(C$_2$H$_5$)$_2$ | 2 | H | |

TABLE 5

| No. | Z | —Y—Q—A | R |
|---|---|---|---|
| 401 | C$_6$H$_5$— | —OCH$_2$—CH$_2$—N(C$_2$H$_5$)$_2$ | H |
| 402 | C$_6$H$_5$— | —OCH$_2$—CH$_2$—N(C$_2$H$_5$)$_2$ | Cl |
| 403 | C$_6$H$_5$— | —OCH$_2$—CH$_2$—N(C$_2$H$_5$)$_2$ | —NH—i-C$_3$H$_7$ |
| 404 | C$_6$H$_5$— | —OCH$_2$—CH$_2$—N(C$_2$H$_5$)$_2$ | OCH$_3$ |
| 405 | 2-thienyl- | —OCH(CH$_3$)—CH$_2$—N(CH$_3$)$_2$ | Cl |
| 406 | 2-thienyl- | —OCH$_2$—CH(CH$_3$)—N(CH$_3$)$_2$ | H |
| 407 | 4-F—C$_6$H$_4$— | —O—(CH$_2$)$_3$—N(CH$_3$)C$_2$H$_5$ | —O—C$_6$H$_5$ |
| 408 | 4-OCH$_3$—C$_6$H$_4$— | —O—(CH$_2$)$_3$—N⟨ ⟩ | —N(CH$_3$)$_2$ |
| 409 | 2-pyridyl- | —SCH$_2$—CH$_2$—N(CH$_2$—CH=CH$_2$)$_2$ | Cl |

TABLE 6

Z—C≡C—Het—Y—Q—A

| No. | Z | —Het— | —Y—Q—A |
|---|---|---|---|
| 451 | C$_6$H$_5$— | (furan-2,5-diyl) | —OCH$_2$—CH$_2$—N(C$_2$H$_5$)$_2$ |
| 452 | 4-F—C$_6$H$_4$— | (thiazole-2,5-diyl) | —OCH$_2$—CH$_2$—N(CH$_3$)$_2$ |
| 453 | 2-thienyl- | (thiazole-2,5-diyl) | —OCH$_2$—CH$_2$—N(CH$_3$)C$_2$H$_5$ |
| 454 | 4-OCH$_3$—C$_6$H$_4$— | (oxazole-2,5-diyl) | —OCH(CH$_3$)—CH$_2$—N(CH$_3$)$_2$ |

TABLE 6-continued
Z—C≡C—Het—Y—Q—A
| No. | Z | —Het— | —Y—Q—A |
|-----|---|-------|--------|
| 455 | C6H5— | 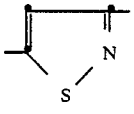 | —OCH2—CH2—N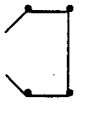 |
| 456 | C6H5— | 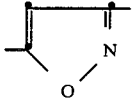 | —OCH2—CH2—N(CH3)2 |
| 457 | 3-OCH3—5-OCH3—C6H3— | 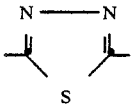 | —O—(CH2)3—N(CH3)C3H7 |
| 458 | 6-Cl—3-pyridyl- | 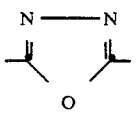 | —OCH2—CH(CH3)—N(CH3)2 |
| 459 | C6H5— | 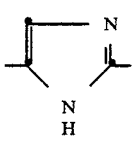 | —OCH2—CH2—N(C2H5)2 |
| 460 | C6H5— | 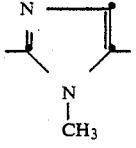 | —OCH2—CH2—N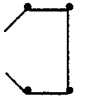 |
| 461 | C6H5— | 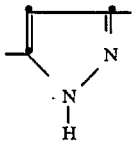 | —OCH2—CH2—N(CH3)2 |
| 462 | 4-CN—C6H4— | 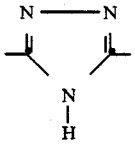 | —OCH2—CH2—N(CH3)2 |
| 463 | 4-F—C6H4— | 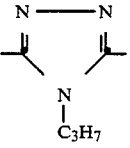 | —OCH(CH3)—CH2—N(C2H5)2 |
| 464 | C6H5— | 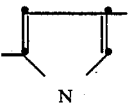 | —OCH2—CH2—N(CH3)2 |
| 465 | C6H5— | 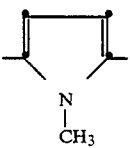 | —O—(CH2)3—N |

TABLE 6-continued

Z—C≡C—Het—Y—Q—A

| No. | Z | —Het— | —Y—Q—A |
|---|---|---|---|
| 466 | C₆H₅— | (triazole ring with N—N, N) | —OCH₂—CH₂—N(CH₃)₂ |
| 467 | 4-F—C₆H₄— | (triazole ring with N, N, N) | —OCH₂—CH₂—N(C₂H₅)₂ |
| 468 | C₆H₅— | (thiophene ring, S) | —OCH₂—CH₂—N(C₂H₅)₂ |
| 469 | 4-F—C₆H₄— | (thiophene ring, S) | —OCH₂—CH₂—N(C₂H₅)₂ |
| 470 | 2-thienyl- | (furan ring, O) | —OCH₂—CH₂—N(CH₃)C₂H₅ |

FORMULATION EXAMPLES

Example 4

Formulation Examples for liquid active ingredients of the formula I (%=percent by weight)

| (a) Emulsion concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 mols of ethylene oxide) | 5% | — | — |
| tributylphenoyl-polyethylene glycol ether (30 mols of ethylene oxide) | — | 12% | 4.2% |
| cyclohexanone | — | 15% | 20% |
| xylene mixture | 70% | 25% | 20% |

Emulsions of the concentration required can be obtained from these concentrates by dilution with water.

| (b) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol (MG 400) | — | 70% | — | — |
| N—methyl-2-pyrrolidone | — | 20% | — | — |
| epoxidised coconut oil | — | — | 1% | 5% |
| benzine (boiling limits 160–190° C.) | — | — | 94% | — |

The solutions are to be applied in the form of very small drops.

| (c) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is applied to the carrier, and the solvent is subsequently evaporated off in vacuo.

| (d) Dusts | a) | b) |
|---|---|---|
| active ingredient | 2% | 5% |
| highly dispersed silicic acid | 5% | 5% |
| talcum | 17% | — |
| kaolin | — | 90% |

Dusts ready for use are obtained by the intimate mixing of the carriers with the active ingredient.

EXAMPLE 5

Formulation Examples for solid active ingredients of the formula I (%=percent by weight)

| (a) Wettable powders | a) | b) |
|---|---|---|
| active ingredient | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol (7–8 mols of ethylene oxide) | — | 2% |
| highly dispersed silicic acid | 5% | 27% |
| kaolin | 67% | — |

The active ingredient is well mixed with the additives and ground in a suitable mill. There are obtained wettable powders which can be diluted with water to give suspensions of the concentration required.

| (b) Emulsion concentrates | | |
|---|---|---|
| active ingredient | 10% | |
| octylphenolpolyethylene glycol ether (4–5 mols of ethylene oxide) | 3% | |

| (b) Emulsion concentrates | |
|---|---|
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| (c) Dusts | (a) | (b) |
|---|---|---|
| active ingredient | 5% | 8% |
| talcum | 95% | — |
| kaolin | — | 92% |

Dusts ready for use are obtained by mixing the active ingredient with the carriers, and grinding the mixture in a suitable mill.

| (d) Extruder granulates | |
|---|---|
| active ingredient | 10% |
| sodium lignin sulfonate | 2% |
| carboxymethylcellulose | 1% |
| kaolin | 87% |

The active ingredient is mixed with the additives, and the mixture is then ground and moisted with water. The mixture is extruded and subsequently dried in a stream of air.

| (e) Coated granulates | |
|---|---|
| active ingredient | 3% |
| polyethylene glycol | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrates | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32.0% |

The finely ground active ingredient is intimately mixed with the additives. There is thus obtained a suspension concentrate from which can be produced, by dilution with water, suspension of the concentration required.

BIOLOGICAL EXAMPLES

Example 6

Post-emergence, herbicidal action (contact herbicide)

Both monocotyledonous and dicotyledonous weeds were sprayed after emergence (in the 4- to 6-leaf stage) with an aqueous active-ingredient dispersion in a dosage of 4 kg of active ingredient per hectare, and were then kept at 24°–26° C. with 45–60% relative humidity. The test results were evaluated 19 days after the treatment, and an assessment was made according to the following scale of ratings:

1: plants totally destroyed,
2–3: very intense action
4–6: medium action
7–8: slight action
9: no action (as untreated control plants).

Post-emergence action

Applied amount: 4 kg of active ingredient/hectare

| Comp. No. | Setaria | Solanum | Sinapis | Stellaria |
|---|---|---|---|---|
| 1 | 4 | 2 | 2 | 3 |
| 3 | 6 | 2 | 2 | 3 |
| 4 | 4 | 1 | 1 | 1 |
| 5 | 2 | 1 | 1 | 1 |
| 6 | 7 | 1 | 1 | 3 |

Example 7

Verification of selectivity with post-emergence application

With the same test procedure, a largish number of cultivated plants and weeds were treated with various applied amounts of active substance per hectare. The test results were evaluated after 19 days on the basis of the scale of ratings given in Example 6.

| Post-emergence action: Compound No. 4 | | | |
|---|---|---|---|
| | Applied amount of active ingredient/hectare | | |
| Test plant | 2 | 1 | 0.5 |
| wheat | 8 | 9 | 9 |
| maize | 8 | 9 | 9 |
| upland rice | 9 | 9 | 9 |
| Alopecurus myos. | 2 | 3 | 8 |
| Rottboellia ex. | 6 | 8 | 9 |
| Abutilon | 1 | 1 | 1 |
| Xanthium Sp | 1 | 2 | 2 |
| Chenopodium Sp. | 2 | 2 | 3 |
| Ipomoea | 1 | 1 | 1 |
| Sinapis | 1 | 1 | 1 |
| Galium aparine | 1 | 2 | 2 |
| Viola tricolor | 3 | 3 | 3 |

What is claimed is:

1. A compound of the formula

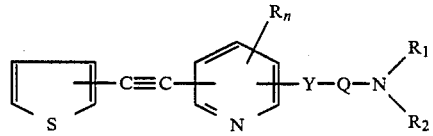

wherein
R is cyano, $C_1$–$C_4$-alkoxy, di-($C_1$–$C_6$-alkyl) amino, halogen or $C_1$–$C_4$-alkyl,
n is 0, 1 or 2,
Y is oxygen or sulfur,
Q is straight-chain or branched-chain $C_2$–$C_6$-alkylene,
each of $R_1$ and $R_2$ is $C_1$–$C_6$-alkyl, $C_3$–$C_6$-alkenyl, $C_3$–$C_6$-alkynyl or $C_3$–$C_8$-cycloalkyl.

2. A compound according to claim 1 in which

R is cyano, methoxy, dimethylamino, fluorine, chlorine or $C_1$-$C_3$-alkyl, each of $R_1$ and $R_2$ is $C_1$-$C_4$-alkyl, allyl, propargyl, cyclopropyl, cyclopentyl or cyclohexyl.

3. A compound according to claim 2 in which

Y is oxygen, in the group Q, the direct alkylene bridge between Y and the nitrogen atom has 2 or 3 carbon atoms, and each of $R_1$ and $R_2$ is methyl or ethyl.

4. A compound according to claim 2 in which

R is cyano or chlorine n is 0 or 1,

Q is $C_2$ or $C_3$-alkylene having 2 carbon atoms in the direct alkylene bridge between Y and the nitrogen atom, each of $R_1$ and $R_2$ is $C_1$-$C_3$-alkyl.

5. A compound according to claim 4 of the formula

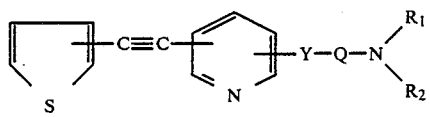

in which each of $R_1$ and $R_2$ is methyl or ethyl.

6. A compound according to claim 1, wherein the direct alkylene bridge between Y and the nitrogen atom consists of 2 or 3 carbon atoms.

7. A compound according to claim 1, wherein $R_1$ and $R_2$ are methyl or ethyl.

8. A compound according to claim 1, wherein Y is oxygen.

9. The compound: 1-[5-(2-thienylethynyl)-pyridyl-2-oxy]-2-diethylaminoethane according to claim 1.

10. A compound according to claim 2, wherein Q contains 2 carbon atoms.

11. A herbicidal composition which comprises an effective amount of at least one compound according to claim 1, together with a suitable carrier therefor.

12. A method of controlling weeds, which method comprises applying thereto or to the locus thereof a herbicidally effective amount of a compound according to claim 1.

13. A method according to claim 12 for selectively controlling weeds in crops of cultivated plants, which method comprises applying the compound post-emergence.

14. A method according to claim 13 for controlling weeds in crops of cereals, maize and rice.